United States Patent
Boehm

(10) Patent No.: US 7,291,479 B2
(45) Date of Patent: Nov. 6, 2007

(54) METHOD FOR DETECTING THE VON WILLEBRAND FACTOR-CLEAVING PROTEASE ACTIVITY OF ADAMTS-13

(75) Inventor: Martina Boehm, Frankfurt (DE)

(73) Assignee: Dade Behring Marburg GmbH, Marburg (DE)

( * ) Notice: Subject to any disclaimer, the term of this patent is extended or adjusted under 35 U.S.C. 154(b) by 365 days.

(21) Appl. No.: 10/519,824

(22) PCT Filed: Jul. 3, 2003

(86) PCT No.: PCT/EP03/07080

§ 371 (c)(1),
(2), (4) Date: Dec. 30, 2004

(87) PCT Pub. No.: WO2004/005451

PCT Pub. Date: Jan. 15, 2004

(65) Prior Publication Data

US 2005/0239153 A1 Oct. 27, 2005

(30) Foreign Application Priority Data

Jul. 3, 2002 (DE) ............................... 102 35 348

(51) Int. Cl.
*C12Q 1/37* (2006.01)
*C12P 21/04* (2006.01)
(52) U.S. Cl. ........................................ 435/23; 435/69.6
(58) Field of Classification Search .................... None
See application file for complete search history.

(56) References Cited

U.S. PATENT DOCUMENTS

2001/0006773 A1   7/2001   Patzke et al. ................... 435/2

FOREIGN PATENT DOCUMENTS

| DE | 199 64 109 A1 | 7/2001 |
| EP | 0 080 614 A2 | 6/1983 |
| EP | 0 227 054 A2 | 7/1987 |
| EP | 0 246 446 A2 | 11/1987 |
| WO | WO 00/50904 A1 | 2/2000 |
| WO | WO 02/10437 A2 | 2/2002 |
| WO | WO 02/42441 A2 | 5/2002 |

OTHER PUBLICATIONS

Boehm, Martina M. et al.: "Von Willebrand Factor-cleaving protease activity in TTP using a new method based on the positive correlation between vWF multimeric size and Ristocetin Cofactor activity" BLOOD: vol. 98, No. 11 Part 1, Nov. 16, 2001, p. 33a XP16. Nov. 16, 2001, p. 33a, XP009022213; 43rd Annual Meeting of the American Society of Hematology, Part 1;Orlando, Florida, Dec. 7-11, 2001, ISSN: 0006-4971 Abstract.
Boehm, Martina M. et al.: "Evaluation and clinical application of a new method for measuring activity of von Willebrand factor-cleaving metalloprotease (ADAMTS13)" Annals of Hermatology: vol. 81, No. 8, Aug. 2002, pp. 430-435, XP002263599; ISSN:0939-5555 (the whole document).
Furlan Miha et al.: "Assays of von Willebrand factor-cleaving protease: A test for diagnosis of familial and acquired thrombotic thrombocytopenic purpura" Seminars in Thrombosis and Hemostasis: vol. 28, No. 2, Apr. 2002, pp. 167-172, XP009022244; ISSN: 0094-6176 (the whole document).
Ewenstein B. M.: "Use of ristocetin cofactor acativity in the management of von Willebrand disease" Haemophilia: The Official Journal of the World Federation of Hemophilia; England; vol. 7, Suppl 1, Jan. 2000, pp. 10-15, XP002263600; ISSN: 1351-8216 (the whole document).
Krizek Dennis M et al: "Clinical application of a rapid method using agarose gel electrophoresis and Western blotting to evaluate von Willebrand factor protease activity" ELECTROPHORESIS vol. 22, No. 5, Mar. 2001, pp. 946-949, XP002263601; ISSN: 0173-0835 (the whole document).
Furlan Miha: "von Willebrand factor: molecular size and functional activity" Annals of Hematology: vol. 72, No. 6, 1996, pp. 341-348, Berlin, Germany, XP000922763; ISSN: 0939-5555 (the whole document).
Fijikawa, K., Suzuki, H., McMullen, B., Chung, D. (2001) Purification of human von Willebrand factor-cleaving protease and its identification as a new member of the metalloproteinase family. Blood 98: 1662-1666.
Gerritsen; H.E., Robles, R., Lämmele, B., Furlan, M. (2001) Partial amino acid sequence of purified von Willebrand factor-cleaving protease Blood 98: 1654-1661.
Lvey, G.G., Nichols, W.C., Lian, E.C. Foroud, T., McClintick, J.N., McGee, B.M., Yang, A.Y., Siemieniak, DR., Stark, K.R., Gruppo, R., Sarode, R., Shurin, S.B., Chandrasekaran, V., Stabler, S.P., Sabio, H., Bouhassira, E.E., Upshaw, J.D., Ginsburg, D., Tsai, H.M. (2001) Mutations in a member of the ADAMTS gene family cause thrombotic thrombocytopenic purpura. Nature 413: 488-494.
Furlan, M., Robles, R, Lämmle, B., (1996) Partial purification and characterisation of a protease from human plasma cleaving von Willebrand factor to fragments produced by in vivo proteolysis. Blood 10: 4223-4234.
Tsai, H.M. (1996) Physiologic Cleavage of von Willebrand factor by a Plasma Protease is dependent on its confirmation and requires Calcium ion. Blood 10: 4235-4244.
Obert B, Tout H, Veyradier A, Fressinaud E, Meyer D, Girma JP (1999) Estimation of the Willebrand factor-cleaving protease in plasma using monoclonal antibodies to VWF. Thromb Haemost 82: 1382-1385.

(Continued)

*Primary Examiner*—Ralph Gitomer
*Assistant Examiner*—Bin Shen
(74) *Attorney, Agent, or Firm*—ProPat, L.L.C.

(57) ABSTRACT

The invention relates to a diagnostic method for determining the von Willebrand factor (VWF) cleaving activity of ADAMTS-13 in a test medium during which the test medium is mixed with 0.5 to 5 U/ml of a von Willebrand factor (VWF) that does not contain ADAMTS-13, and after incubation, the ADAMTS-13 activity is determined based on the drop in the VWF-mediated aggregation of thrombocytes.

13 Claims, 3 Drawing Sheets

OTHER PUBLICATIONS

Raife TJ, Atkinsons B, Christopherson P, Jozwiak M, Montgomery RR (2001) Recombinant, truncated monomeric von Willebrand factor (VWF) for the study of VWF proteolysis. Thromb Haemost, Suppl July: Abstract#1667.

Kasper, C.K. (1991) Laboratory tests for factor VIII inhibitors, their variation, significance and interpretation. Blood Coagul Fibrinolysis 2: 7-10.

Boehm, Martina M. et al.: "*Correlation of VWF-Cleaving Protease Activity, WF:AG and Frequency of Relapses in 17 TTP-Patients Observed Between 1982 and 2001*" (Feb. 2002) Zim der J.W. Goethe University Fim (Frankfurt) abstract No. 28.

Boehm, Martina M. et al.: "*The Significance of The VWF-Cleaving Protease in the Pathogenesis of TTP*" (Feb. 2002) Zim der J.W. Goethe University Fim (Frankfurt) abstract No. 29.

Manucci, P.M. et al.: "*Changes in health and disease of the metalloprotease that cleaves von Willebrand factor*" BLOOD: vol. 98, No. 9, Nov. 1, 2001, pp. 2730-2735.

Database BIOSIS at STN; AN 2002:382326: "*Impaired activity of plasma von Willebrand factor-cleaving protease may predict the occurrence of hepatic veno-occlusive disease after stem cell transplantation*", Park, Y.-D. et al., Bone Marrow Transplantation, (May 1, 2002) vol. 29, No. 9, pp. 789-794.

Zheng, X. et al.: "*Structure of von Willebrand Factor-cleaving Protease (ADAMTS13), a Metalloprotease Involved in Thrombotic Thrombocytopenic Purpura*"; Journal of Biological Chemistry (2001) vol. 276, No. 44, pp. 41059-41063.

Poster shown at the 43rd Annual Metting of the American Society of Hematology on Dec. 8, 2001 in Orlando,Florida.

Abstract of the Poster shown at the 43rd Annual Meeting of the American Society of Hematology on Dec. 8, 2001 in Orlando,Florida.

Von Willebrand Factor 2002 Minutes, p. 4 (speech given at the SSC meeting on Jul. 20, 2002 in Boston, USA).

Abstract of a speech given on Nov. 11, 2001 in Hamburg, Germany.

Time [h]:  0    0.5   1.25   2    4    6    7.5   22

RCo [%]:  357  295  313  316  204  134  130  13

METHOD FOR DETECTING THE VON WILLEBRAND FACTOR-CLEAVING PROTEASE ACTIVITY OF ADAMTS-13

CROSS REFERENCE TO RELATED APPLICATIONS

This application is being filed under Rule 1.371 as a National Stage Application of International Application No. PCT/EP2003/007080 filed Jul. 3, 2003, which claims priority to parent German Patent Application No. 102 35 348.4 filed Jul. 3, 2002. The parent application, German Patent Application No. 102 35 348.4 is hereby incorporated by reference herein in its entirety.

FIELD OF THE INVENTION

The invention relates to a diagnostic method for detecting VWF-cleaving ADAMTS-13 activity in blood plasma and other media.

BACKGROUND OF THE INVENTION

Thrombotic thrombocytopenic purpura (TTP) is a disease in which the classical symptoms of thrombocytopenia and microangiopathic, hemolytic anemia, neurological symptoms, disturbances in kidney function, and fever, are observed. Unusually large multimers of the von Willebrand factor (VWF) are found in plasma from TTP patients and are regarded as being the reason for the formation of VWF-rich and platelet-rich thrombi. Endothelial cells release von Willebrand factor in the form of large multimers which, in normal plasma, are cleaved by the combined action of a reductase and a metalloprotease.

In addition, it is already known that patients suffering from congenital or acquired TTP are observed to lack a specific metalloprotease which cleaves VWF between the amino acids Tyr842 and Met843. This metalloprotease has recently been identified as a new member of the ADAMTS (a disintegrin and metalloprotease with thrombospondin motifs) family and designated ADAMTS-13 Fujikawa, K., Suzuki, H., McMullen, B., Chung, D. (2001) Purification of human von Willebrand factor-cleaving protease and its identification as a new member of the metalloproteinase family. Blood 98: 1662-1666 (hereinafter "1"); Gerritsen; H. E., Robles, R., Lämmele, B., Furlan, M. (2001) Partial amino acid sequence of purified von Willebrand factor-cleaving protease Blood 98 : 1654-1661 (hereinafter "2"); Levy, G. G., Nichols, W. C., Lian, E. C. Foroud, T., McClintick, J. N., McGee, B. M., Yang, A. Y., Siemieniak, DR., Stark. K. R., Gruppo, R., Sarode, R., Shurin, S. B., Chandrasekaran. V., Stabler, S. P., Sabio. H., Bouhassira, E. E., Upshaw, J. D., Ginsburg, D., Tsai, H. M. (2001) Mutations in a member of the ADAMTS gene family cause thrombotic thrombocytopenic purpura. Nature 413: 488-494 (hereinafter "3").

In that which follows, the VWF-cleaving protease activity of ADAMTS-13 is simply termed ADAMTS-13 activity. ADAMTS-13 activity is normally measured by incubating a VWF sample, which has been treated with urea or guanidium hydrochloride, with dilute plasma at low ionic strength. The proteolysis is detected by means of a multimer analysis using SDS agarose gel electrophoresis or by means of fragment analysis using SDS polyacrylamide gel electrophoresis and subsequent immunoblotting, that is detecting the proteins on a cellulose membrane by means of an antigen-antibody reaction Furlan, M., Robles, R., Lämmle, B., (1996) Partial purification and characterisation of a protease from human plasma cleaving von Willebrand factor to fragments produced by in vivo proteolysis. Blood 10: 4223-4234 (hereinafter "4"): Tsai, H. M. (1996) Physiologic Cleavage of von Willebrand factor by a Plasma Protease is dependent on its confirmation and requires Calcium ion. Blood 10: 4235-4244 (hereinafter "5"). The ADAMTS-13-catalyzed degradation of the von Willebrand factor can also be determined by measuring the collagen-binding activity of the VWF (WO-A 00/50904) or by carrying out a specific, bilateral ELISA detection Obert B, Tout H. Veyradier A. Fressinaud F, Meyer D, Girma JP (1999) Estimation of the Willebrand factor-cleaving protease in plasma using monoclonal antibodies to VWF. Thromb Haemost 82: 1382-1385 (hereinafter"6"). A recombinant monomeric VWF, which has been labeled at the N terminus with a green fluorescent protein, has also recently been described for the purpose of determining the proteolysis Raife TJ, Atkinsons B, Christopherson P. Jozwiak M, Montgomery RR (2001) Recombinant, truncated monomeric von Willebrand factor (VWF) for the study of VWF proteolysis. Thromb Haemost, Suppl July: Abstract#1667 (hereinafter "7").

The conventional electrophoretic methods can only be carried out in specialized research laboratories since implementing the tests requires special laboratory equipment and the requisite expertise. While the collagen-binding test (WO-A 00/50904) and the specific ELISA (6) for detecting the proteolytic activity of ADAMTS-13 simplify the determination of ADAMTS-13 activity, they can likewise only be carried out in the laboratories which have at their disposal the appropriate equipment and the necessary knowhow. Furthermore, the bilateral ELISA requires specific monoclonal antibodies which are only available in a few laboratories since they cannot be obtained commercially. The object therefore presented itself of developing a simple method for determining ADAMTS-13 activity. This novel method was to make it possible to quantify ADAMTS-13 activity in blood plasma and other body fluids (e.g. blood serum, and saliva), and other media, in a reliable and timely manner. It was to be utilizable in any routine clinical coagulation laboratory and therefore not require any special laboratory equipment, special technical knowhow or reagents which were not available commercially. Furthermore, the novel method was to permit an automation in automatic coagulation machines which was as far reaching as possible in order to make it possible to achieve a high sample throughput at low operational cost. Since it has by now been demonstrated that low ADAMTS-13 activities can also be observed in diseases other than TTP, such a method was to make it possible to differentiate between the severe ADAMTS-13 deficiency which is characteristic of TTP and mild ADAMTS-13 deficiency. Kasper. C. K. (1991) Laboratory tests for factor VIII inhibitors, their variation, significance and interpretation. Blood Coagul Fibrinolysis 2: 7-10 (hereinafter "8") An early diagnosis, and consequently a rapid initiation of plasmapheresis therapy, essentially determines the clinical course of what is frequently a life-threatening TTP episode. For this reason, the novel method was to enable ADAMTS-13 activity to be determined rapidly and as comprehensively as possible. Timely determination of the ADAMTS-13 activity is also essential because of the existence of alternative therapy options. In particular, the method was to enable an inhibitor against ADAMTS-13 to be detected rapidly, or to enable the inhibitor titer to be determined, since different treatment possibilities (e.g. rituximab or immunoadsorption) ensue from this. The method was also, in particular, to make it possible to differentiate between congenital and acquired TTP. In addition to this, timely ADAMTS-13 activity determination, which is capable of being carried out routinely, is the prerequisite for using the recombinant ADAMTS-13 which is potentially available (W0242441). The method was not only to permit timely diagnosis, and monitoring of the therapy, of TTP patients but, in addition, reliable quantification of the ADAMTS-13 activity in any arbitrary media. Since ADAMTS-13 is an important regulator of VWF, and consequently a significant factor in hemostasis, the novel method was to be applicable in diverse studies of the importance of ADAMTS-13-catalyzed proteolysis of VWF in healthy subjects and patients suffering from different diseases.

SUMMARY OF THE INVENTION

It has now been found, surprisingly, that the ADAMTS-13-catalyzed proteolysis of VWF can be detected by the ability of the VWF to aggregate platelets. The cleavage of the VWF by ADAMTS-13 results in the VWF multimers being truncated. The ability of the VWF to aggregate platelets is essentially determined by the length of the multimers. The larger the VWF multimers are, the greater is their capacity for binding platelets. In the method according to the invention, this correlation was exploited in order to determine ADAMTS-13 activity.

DETAILED DESCRIPTION OF THE INVENTION

The invention accordingly relates to a diagnostic method for determining the VWF-cleaving activity of ADAMTS-13 in a test medium, in which from 0.5 to 5 U of an ADAMTS-13-free von Willebrand factor (VWF) is/are added, per ml, to the test medium and, after incubation, the ADAMTS-13 activity is determined by way of the reduction in the VWF-mediated aggregation of platelets.

Within the meaning of the invention, "test medium" refers to all body fluids, such as blood plasma, blood serum, saliva and cerebrospinal fluid, and other test media, such as cell culture supernatants or cell extracts.

An ADAMTS-13-free VWF, which is termed VWF substrate below, is added to the test medium. The VWF substrate employed is preferably a highly purified plasmatic VWF which exhibits the multimer pattern typical for normal plasma and which is free from endogenous ADAMTS-13 activity. However, it is also possible to use a variety of other VWF substrates which do not exhibit any ADAMTS-13 activity, such as recombinant VWF, VWF from cell culture supernatants or plasmatic VWF in which the ADAMTS-13 activity has been irreversibly inhibited.

Figure 1A:
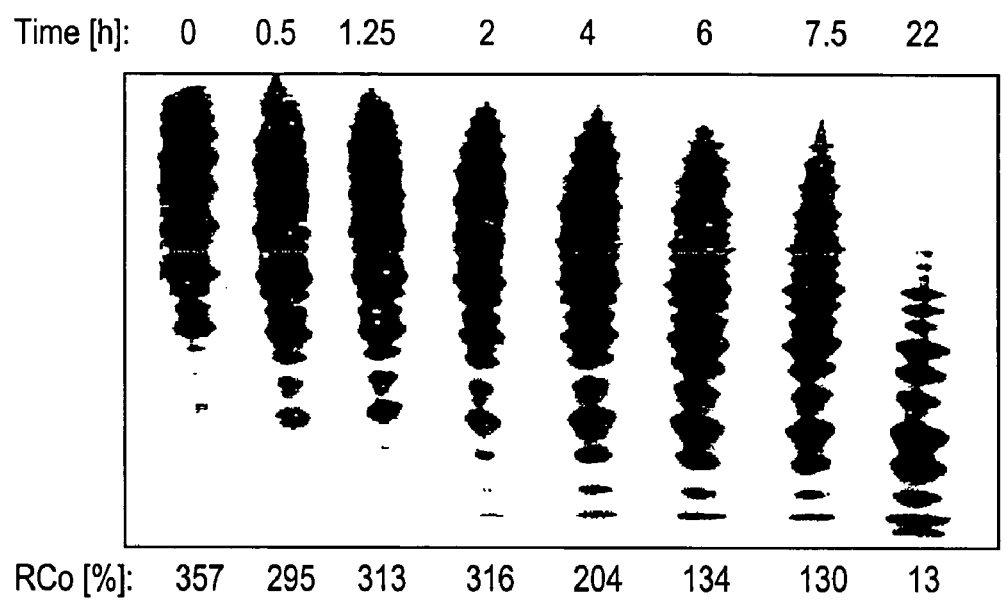
FIG. 1a is an exemplary multimer pattern illustrating the time-dependent loss of the high molecular weight VWF multimers as a reuslt of ADAMTS-13-catalyzed proteolysis.
Figure 1B:
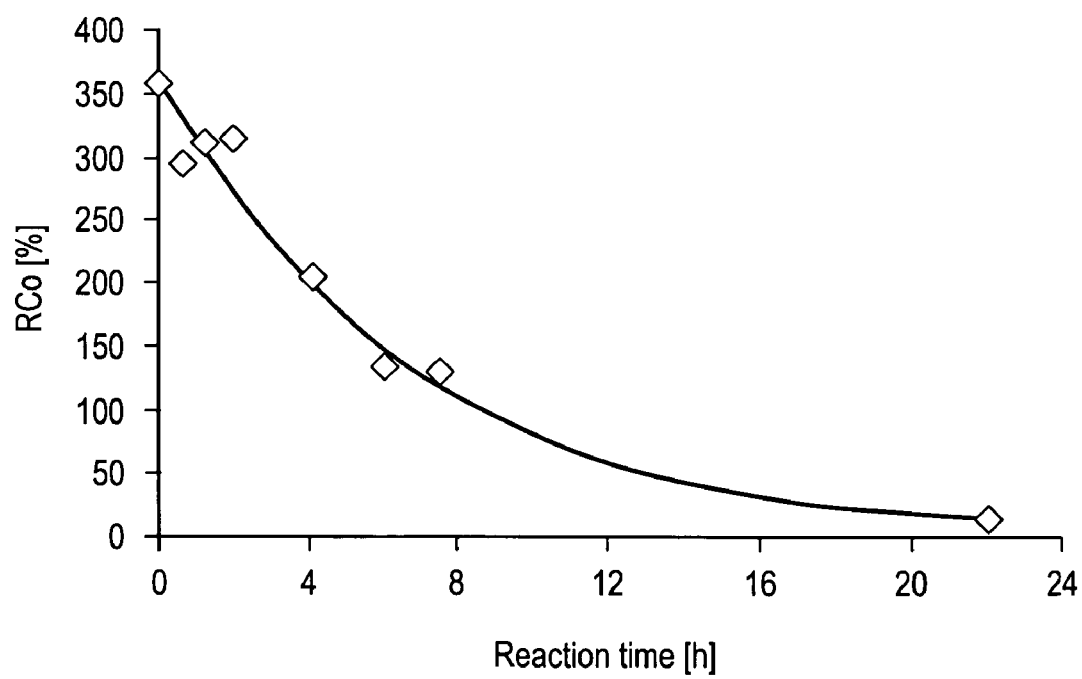
FIG. 1b is a graphical illustration of the ADAMTS-13-catalyzed loss over time of the RCo activity of the VWF substrate which has been added to the reaction medium.

The typical multimer pattern of a highly purified plasmatic VWF is shown in the first column in FIG. 1A. The following 7 columns show the time-dependent loss of the high molecular weight VWF multimers as a result of ADAMTS-13-catalyzed proteolysis. For this, a sample was in each case removed from a test mixture after the incubation times (0.5-22 h) indicated in FIG. 1A and the reaction was stopped by adding EDTA. The samples were then fractionated by SDS agarose gel electrophoresis, in accordance with customary standard methods, and subsequently visualized by immunoblotting. In addition, a sample was in each case removed from the reaction mixture after the corresponding incubation times for the purpose of determining the functional activity of the VWF. For this, the ability of the VWF to aggregate blood platelets in the presence of ristocetin was determined; this ability is commonly termed the ristocetin cofactor (RCo) activity. The RCo activity was determined using the commercially available BC von Willebrand reagent supplied by Dade Behring (Marburg, Germany). The RCo activities, which were thus measured, of the corresponding samples are given under the columns of the immunoblot shown in FIG. 1A. It can be seen that the time-dependent ADAMTS-13-catalyzed loss of the high molecular weight VWF multimers leads to a marked loss of RCo activity, i.e. from 357% at the beginning of the reaction down to 13% after an incubation period of 22 hours. FIG. 1B illustrates once again this time-dependent ADAMTS-13-catalyzed loss of the RCo activity of the VWF substrate which has been added to the reaction medium.

Figure 2:
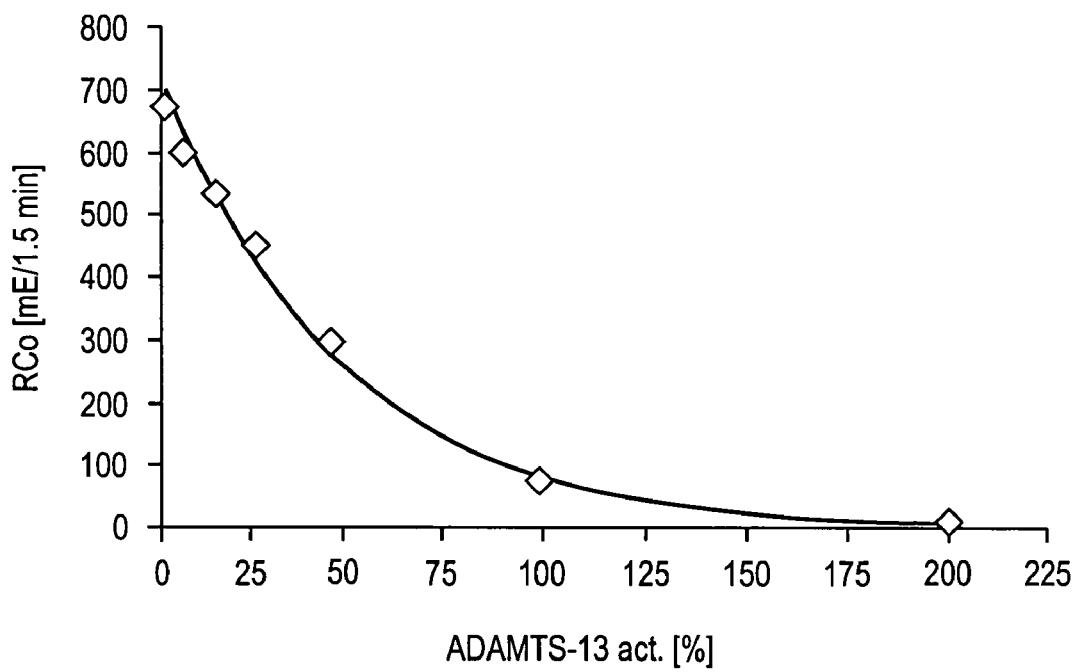
FIG. 2 is a graphical illustration of the ability of a given sample to aggregate platelets in the presence of ristocetin, as measured by the decrease in extinction in 90 seconds, for different dilutions of normal human plasma.

In general, the procedure in the method according to the invention is that the diluted test medium, e.g. blood plasma, is added to 0.5-5 U, preferably 1-3 U, of an ADAMTS-13-free von Willebrand factor (VWF) per ml. In this connection, the test medium should be so dilute that the endogenous VWF can be disregarded, i.e. it does not induce any detectable platelet aggregation. The ADAMTS-13-free VWF and the dilute test medium are then incubated for a time, preferably 0.1-24 hours, particularly preferably 6-15 hours, which is sufficiently long. According to available investigation results, it even appears possible to reduce the incubation time down to 0.5-6 minutes, preferably from 1 to 3 minutes. This incubation is expediently effected in a low molar reaction buffer (e.g. 5-20 mmol of TRIS-HCl/l, pH 8) and preferably in the presence of divalent cations, e.g. $Ba^{2+}$ or $Ca^{2+}$, of a serine protease inhibitor, e.g. PefaBlocSC, and urea. The preferred concentration of divalent cations in the reaction medium is from 5 to 15 mmol/l, particularly preferably 7-9 mmol/l. The preferred concentration of Pefabloc in the reaction medium is from 0.5 to 6.5 mmol/l, particularly preferably 0.75 mmol/l. The preferred concentration of urea in the reaction medium is from 0.5 to 3 mol/l, particularly preferably 1.5 mol/l. At the end of the adequate incubation, the remaining ability of the VWF substrate to aggregate platelets is determined. This can, for example, be measured by way of the ristocetin cofactor activity (which describes the VWF-mediated aggregation of the platelets in the presence of ristocetin), preferably using the commercially available BC von Willebrand reagent supplied by Dade Behring (Marburg, Germany) with the determination preferably being automated and taking place in an automatic coagulation machine. For this, determined quantities of platelets and ristocetin are added to the reaction medium. The preferred concentration of blood platelets in the test mixture is from 1 000 000 to 100 000 platelets/ul, particularly preferably from 500 000 to 200 000 platelets/µl. The preferred concentration of ristocetin in the test mixture is from 0.5 to 3 mg/ml, particularly preferably from 1 to 2 mg/ml. In the presence of ristocetin, the VWF substrate in the reaction medium causes the platelets to aggregate. The aggregation which is taking place reduces the turbidity of the reaction mixture. It is consequently possible, by measuring the optical density, to quantify the ability of the VWF substrate to aggregate platelets. The ristocetin cofactor activity of the VWF substrate which remains in the reaction medium, as determined in this way, depends on the ADAMTS-13 activity in the test medium. The more ADAMTS-13 activity which is present in the test medium, the more will the added VWF substrate be broken down and lose its ability to aggregate platelets. Normal human plasma, which has been diluted with varying quantities of inactivated (it is the activity of ADAMTS-13 which has been inactivated) normal human plasma, is used for calibration. The inactivation can, for example, be effected by means of heating. This correlation is depicted in FIG. 2. The x axis shows the different dilutions of the normal human plasma (1:21 dilution=100%). The y axis shows the ability of the corresponding sample to aggregate platelets in the presence of ristocetin, as measured by the decrease in extinction in 90 seconds (mE/1.5 min). The dilution of the normal plasma leads to a limited loss of ADAMTS-13 activity in the test sample, with the 1:21 dilution being defined as 100%. Under the conditions of the method according to the invention, the content of ADAMTS-13 in the test medium determines the ristocetin cofactor activity of the substrate in the reaction medium. The correlation between ADAMTS-13 activity in the test medium and ristocetin cofactor activity in the reaction medium can be described by an equation of the following type: $y=A+(D-A)/(1+e^{(B*(c-x))})$, (calculated using Easy fit, version 5.14, software from Tecan, Basle, Switzerland). The determination of VWF ristocetin cofactor activity normally takes place in plasma (DE 199 64 109 A 1) and is a common and rapid test in any well-equipped routine coagulation laboratory. The successful use of the test in the method according to the invention is particularly surprising since, in this case, the RCo activity of a VWF substrate is measured in a very unphysiological reaction medium containing a low buffer concentration and in the presence of a serine protease inhibitor and urea. The RCo activity test is normally used for determining the RCo activity in a given plasma sample. Instead of this, the plasma (or the corresponding test medium) is diluted to such an extent, in the method according to the invention, that the endogenous VWF can no longer induce any detectable aggregation of the platelets, i.e. the endogenous RCo activity is <2.5%. An exogenous ADAMTS-13-free VWF is added, under the described conditions, to the plasma which has been diluted in this way, with the VWF being broken down by the ADAMTS-13 activity in the diluted plasma sample. The breakdown of the exogenous VWF substrate is quantified by determining the RCo activity. The novel use of a known, widespread test, which is capable of being performed routinely, in the method according to the invention makes it possible to employ the method in any well-equipped routine coagulation laboratory.

In a simplified manner, the method according to the invention can be described as the ADAMTS-13 which is present in the test medium acting on an ADAMTS-13-free VWF substrate and thereby altering the activity of the VWF (truncation of the VWF multimers)

measuring the altered VWF activity by determining the VWF-mediated aggregation of platelets in the presence of ristocetin equating the extent of the reduction in the activity of the VWF with the ADAMTS-13 activity in the test medium.

However, the method according to the invention can also be reversed:

aggregating platelets with ADAMTS-13-free VWF in the presence or absence of ristocetin incubating with test medium which contains ADAMTS-13 thereby altering the activity of the VWF, with this leading to dissociation of the platelet aggregates equating the extent of the dissociation with the ADAMTS-13 activity in the test medium.

In a special embodiment of the method according to the invention, the ADAMTS-13-free VWF substrate can also be associated with a solid phase, for example a microtiter plate or a microparticle, for example by way of a specific binding partner.

Within the meaning of this invention, the term "solid phase" constitutes an article which is composed of porous and/or nonporous, as a rule water-insoluble, material and which can have a very wide variety of forms, such as a vessel, a tube, a microtitration plate, a sphere, a microparticle, a rod, strips, filter paper, chromatography paper, etc. As a rule, the surface of the solid phase is hydrophilic or can be made hydrophilic. The solid phase can be composed of a very wide variety of materials, such as inorganic and/or organic materials, and be composed of synthetic materials, naturally occurring materials and/or modified naturally occurring materials. Examples of solid phase materials are polymers, such as cellulose, nitrocellulose, cellulose is acetate, polyvinyl chloride, polyacrylamide, crosslinked dextran molecules, agarose, polystyrene, polyethylene, polypropylene, polymethacrylate or nylon; ceramic; glass; metals, in particular precious metals such as gold and silver; magnetite; mixtures or combinations thereof; etc. Cells, liposomes and phospholipid vesicles are also encompassed by the term solid phase.

The solid phase can have a coating composed of one or more layer(s), for example composed of proteins, carbohydrates, lipophilic substances, biopolymers, organic polymers, or mixtures thereof, in order, for example, to suppress or prevent the nonspecific binding of sample constituents to the solid phase, or in order, for example, to achieve improvements with regard to the suspension stability of particulate solid phases, storage stability, shape stability or resistance to UV light, microbes or other agents having a destructive effect.

Within the meaning of this invention, the term "microparticles" is to be understood as meaning particles which have an approximate diameter of at least 20 nm and not more than 20 µm, usually between 40 nm and 10 µm, preferably between 0.1 and 10 µm, particularly preferably between 0.1 and 5 µm, very particularly preferably between 0.15 and 2 µm. The microparticles can have a regular or irregular shape. They can constitute spheres, spheroids or spheres having cavities or pores of larger or smaller size. The microparticles can be composed of organic material, of inorganic material or of a mixture or combination of the two. They can be composed of a porous or nonporous material and of a swellable or nonswellable material. In principle, the microparticles can be of any density; however, preference is given to particles having a density which approaches the density of water, for example from about 0.7 to about 1.5 g/ml. The preferred microparticles can be suspended in aqueous solutions and the suspension is stable for as long as possible. The microparticles may be transparent, partially transparent or nontransparent. The microparticles can be composed of several layers, such as what are termed core-and-shell particles, having a core and one or more enveloping layer(s). The term microparticle encompasses, for example, dye crystals, metal sols, silica particles, glass particles, magnetic particles, particles containing chemoluminescent and/or fluorescent substances, polymer particles, oil drops, lipid particles, dextran and protein aggregates. Preferred microparticles can be suspended in aqueous solutions and are particles which are composed of water-insoluble polymer material, in particular of substituted polyethylenes. Very particular preference is given to latex particles, for example composed of polystyrene, acrylic acid polymers, methacrylic acid polymers, acrylonitrile polymers, acrylonitrile butadiene styrene, polyvinyl acetate acrylate, polyvinylpyridine or vinyl chloride acrylate. Latex particles possessing reactive groups at their surface, such as carboxyl groups, amino groups or aldehyde groups, which enable specific binding partners, for example, to be bonded covalently to the latex particles, are of particular interest. The preparation of latex particles is described, for example, in EP 0 080 614, EP 0 227 054 and EP 0 246 446.

A microparticle can have a coating composed of one or more layer(s), for example composed of proteins, carbohydrates, biopolymers or organic polymers, or mixtures thereof, in order, for example, to suppress or prevent non-specific binding of sample constituents to the particle surface or in order, for example, to achieve improvements with regard to the suspension stability of the microparticles, the shape stability, or the resistance to UV light, microbes and other agents having a destructive effect. Thus, this coating can, in particular, be composed of protein layers or polymer layers, such as cyclodextrins, dextrans, hydrogels, albumin or polyalbumins, which have, for example, been applied covalently or adsorptively to the microparticles.

The term "associated" encompasses, for example, a covalent and a noncovalent bond, a direct and an indirect linkage, adsorption to a surface and inclusion in a recess or a cavity, etc. Usually, a covalent bond is said to exist between two molecules when at least one atomic nucleus of one of the molecules shares electrons with at least one atomic nucleus in the second molecule. Examples of a noncovalent bond are surface adsorption, inclusion in cavities or the binding of two specific binding partners. In addition to a direct linkage, the object to be bound can also be bound indirectly to the solid phase by way of a specific interaction with specific binding partners.

A "specific binding partner" is to be understood as being a member of a specific binding pair. The members of a specific binding pair are two molecules which in each case possess at least one structure which is complementary to a structure possessed by the other molecule, with the two molecules being able to bind to each other by way of a bond formed by the complementary structures. The term molecule also encompasses molecular complexes, such as enzymes which are composed of an apoenzyme and a coenzyme, proteins which are composed of several subunits, lipoproteins, which are composed of proteins and lipids, etc. While specific binding partners can be naturally occurring, they can also be substances which are prepared, for example, by means of chemical synthesis, microbiological techniques and/or recombinant methods. For the purpose of illustrating the term specific binding partner, but without this being understood as a limitation, the following examples may be mentioned: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, etc. Examples of specific binding pairs are: antibody-antigen, antibody-hapten, operator-repressor, nuclease-nucleotide, biotin-avidin, lectin-polysaccharide, steroid-steroid-binding protein, active compound-active compound receptor, hormone-hormone receptor, enzyme-substrate, IgG-protein A, complementary oligonucleotides or polynucleotides, etc.

In another embodiment of the method, the latter can also be carried out under the influence of shearing forces, for example in a flowing medium.

The invention furthermore relates to a diagnostic kit which contains an ADAMTS-13-free VWF substrate, platelets and, where appropriate, ristocetin.

The invention furthermore relates to the use of a reagent for detecting VWF activity for the purpose of detecting ADAMTS-13 activity.

The invention is explained in more detail below with the aid of examples:

EXAMPLES

The method according to the invention was compared in detail with the immunoblotting method which has been employed previously. The diagnostic method according to the invention was used for determining ADAMTS-13 activity in 14 TTP patients during acute attacks, during the course of therapy and in remission; in addition, it was used for determining ADAMTS-13 activity in 80 healthy test subjects as well as in 23 patients suffering from thrombocytopenia and/or hemolysis and in 14 patients suffering from antiphospholipid syndrome (APS).

1. Plasma Samples

Citrate-treated plasma samples were obtained, prior to plasma substitution with freshly frozen plasma, from 14 patients in connection with 22 acute TTP attacks. The initial diagnosis was based on clinical symptoms (especially neurological disturbances) and laboratory findings such as severe thrombocytopenia and the detection of microangiopathic hemolytic anemia. Plasma samples were also obtained from 11 patients who were in remission. Blood was also obtained from 10 patients during plasma substitution therapy. Plasma samples from 23 patients suffering from acute thrombocytopenia and/or hemolysis, 14 patients suffering from antiphospholipid syndrome and 80 healthy test subjects were also analyzed. Platelet-depleted plasma was prepared by centrifuging at 2500 g for 40 minutes at 4° C. The supernatant was then stored at −20° C. until used.

2. Using the Method According to the Invention to Determine ADAMTS-13 Activity

Plasma samples were diluted 1:21 with 5 mM Tris-HCl buffer, pH 8, which contained 12.5 mM barium chloride ($BaCl_2$) and 1 mM PefaBloc SC, a serum protease inhibitor (AppliChem GmbH, Darmstadt, Germany), and then incubated at 37°C. for 5 minutes in order to activate the protease. A purified VWF (Concendre de Facteur Willebrand Humain Tres Haute Purite, LFB France) was used as substrate. The concentrate, which was free from detectable ADAMTS-13 activity, was reconstituted with water for injection to a concentration of 100 U/ml, aliquoted out and stored at −20°C. until use. Prior to the protease acting on it, the substrate was thawed, diluted, in a ratio of 1:20, with 5 M urea in 5 mM Tris-HCl, pH 8, and incubated at room temperature for 5 minutes. 100 µl of the substrate solution were then added to 210 µl of diluted plasma and the whole was left to react overnight at 37° C. After that, the residual ristocetin cofactor activity of the added VWF substrate was determined in the reaction medium using the commercial BC von Willebrand reagent supplied by Dade Bebring (Marburg, Germany). The ADAMTS-13 activity in a plasma mixture which was obtained from 80 evidently healthy adult subjects, and which was diluted 1:21, was defined as being 100%. For calibration, serial dilutions of the plasma pool of from 1:2 to 1:32 were prepared using heat-treated plasma pools. For the heat treatment, the plasma pool was incubated at 60°C. for 30 min and then centrifuged at 13 000 rpm for 5 min (Biofuge A, Heraeus) in order to sediment protein aggregates. The plasma which had been treated in this way did not contain any detectable ADAMTS-13 activity. The different dilutions consequently contained defined percentage quantities of ADAMTS-13 activity. The calibration curve which was obtained in this way is depicted in FIG. 2. The different dilutions of the normal plasma pool, which by definition contain from 200 to 0% ADAMTS-13 activity, are plotted on the x axis. The y axis shows the ability of the corresponding sample to aggregate platelets in the presence of ristocetin, as measured by the decrease in extinction during the measurement time of 90 seconds (mE/1.5 min).

3. Using the Immunoblotting Method to Determine ADAMTS-13 Activity (comparison example)

Figure 3:
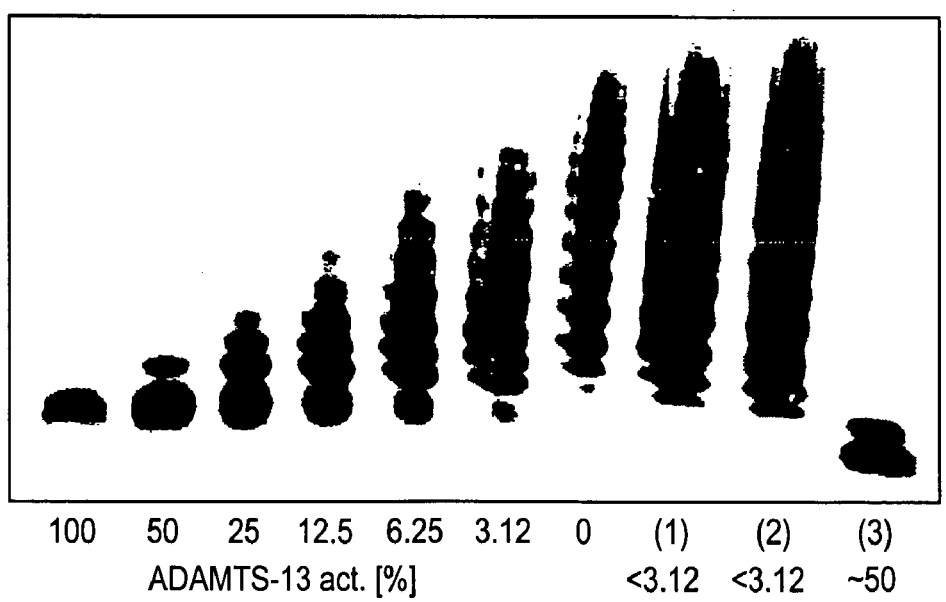
FIG. 3 illustrates the results of an exemplary test using an immunoblotting method in accordance with the invention.

A variant of the method which was first described by Furlan et al. and Tsai (4, 5) was used for measuring ADAMTS-13 activity by the immunoblotting method. Plasma samples were diluted, in a ratio 1:5, with 5 mM Tris buffer, pH 8, including 12.5 mM $BaCl_2$ and 1 mM PefaBloc SC, and the activation, and the action, of the protease were carried out in the same way as described for the method according to the invention. The reaction was stopped by adding disodium EDTA to a final concentration of 23.5 mM. The multimer analysis was carried out by means of SDS electrophoresis on a 1.4% agarose (Seakem HGT from Biozym Diagnostics, Hess, Oldenburg, Germany), and a peroxidase-conjugated anti-VWF antibody (P0226 from Daka-Glostrup, Denmark) was used for the immunoblotting. For quantitative determination, serial dilutions of normal plasma were tested as already described above. The results of an exemplary test using the immunoblotting method are depicted in FIG. 3. For calibration, various dilutions (from 1:5 to 1:160) of a normal human plasma were treated with VWF substrate. By definition, the dilutions contain from 100 to 0% ADAMTS-13 activity (columns 1-7; 1:5 dilution =100%). Columns 8-10 show plasma samples from TTP patients. The ADAMTS-13 activity of the test samples is assessed using the calibration in columns 1-7.

4. Inhibitor Test

The method according to the invention can also be used for determining inhibitory activity against ADAMTS-13. Determining inhibitory activity against ADAMTS-13 is, in particular, of crucial clinical importance for distinguishing between congenital and acquired TTP. Furthermore, detecting an inhibitor, or determining the titer of the inhibitor, is essential for reaching a decision with regard to alternative therapy options (e.g. rituximab or immunoadsorption). For the purpose of testing inhibitory activity against ADAMTS-13, plasma samples, either undiluted or diluted with heat-treated plasma pool, were mixed with equal quantities of normal plasma. For comparison, the normal plasma was mixed 1:1 with heat-treated plasma pool. After a 30 minute incubation at 37° C., the ADAMTS-13 activity in the mixtures was determined using the method according to the invention or using the immunoblotting method which has thus far been customary. The ADAMTS-13 activity in the test sample was divided by the activity of the comparison mixture and multiplied by 100 in order to determine the residual ADAMTS-13 activity. For quantitative determination, samples having a residual activity of from 25 to 75% were selected and the quantity of inhibitor was determined as described for inhibitors of blood coagulation factor VIII (8). By definition, a sample causing a 50% inhibition of the normal ADAMTS-13 activity contained 1 U of inhibitor/ml.

5. Results

Accuracy and Reproducibility of the Method According to the invention

Figure 4:
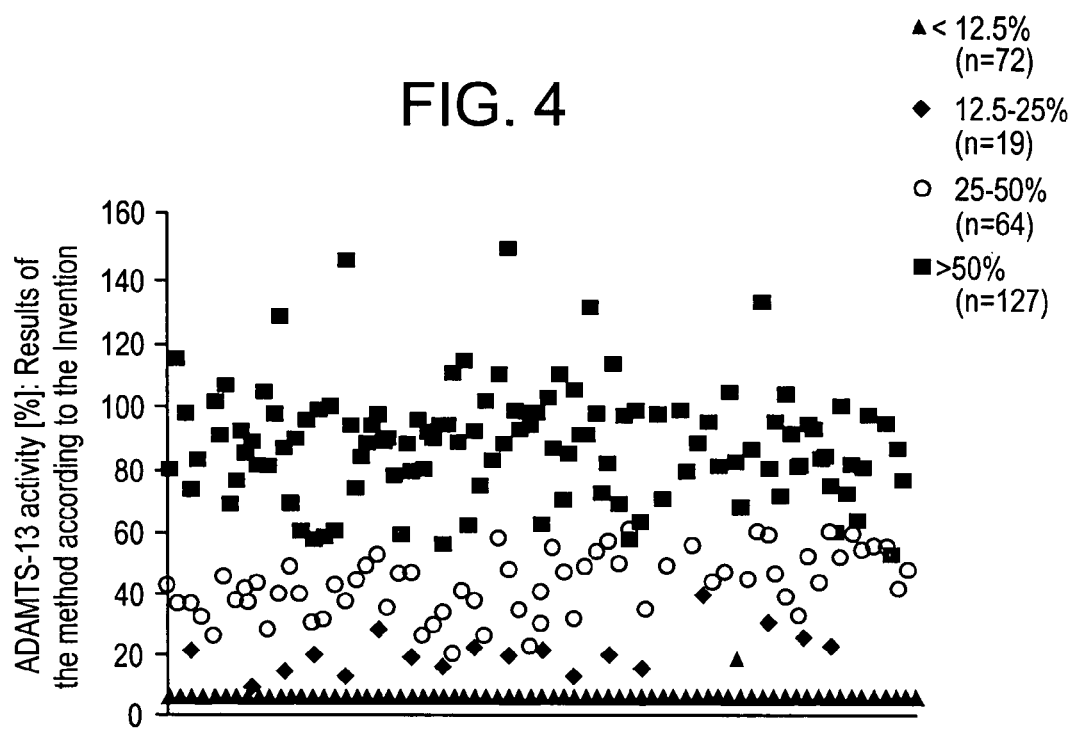
FIG. 4 is a graphical illustration of the ADAMTS-13 activity and associated immunoblotting category for plasma samples taken from numerous patients and healthy subjects.

The accuracy of the method according to the invention was proved by testing 282 plasma samples from patients and healthy subjects both in accordance with the conventional immunoblotting method and in accordance with the method according to the invention. The results are shown in FIG. 4. In this experiment, the results of the immunoblotting method are divided into the following categories: severe ADAMTS-13 deficiency at activities of <12.5% (triangles), moderately severe ADAMTS-13 deficiency with activities between 12.5 and 25% (diamonds), slight ADAMTS-13 deficiency with activities between 25 and 50% (circles) and normal ADAMTS-13 activity with activities >50% (squares). The results obtained with the method according to the invention for the corresponding samples are shown on the y axis. In 71 out of 72 samples of severe ADAMTS-13 deficiency, the same results were found using both methods. In the case of one sample from a TTP patient during plasmapheresis therapy, an activity of from 0 to 12.5% was measured in the immunoblotting method while the same sample gave an activity of 18% in the method according to the invention. The 19 samples which indicated moderately severe ADAMTS-13 deficiency in accordance with the immunoblotting method gave ADAMTS-13 activities of between 9 and 39% in the method according to the invention. In the case of the 64 samples indicating slight protease deficiency in accordance with the immunoblotting method, the method according to the invention measured activities of between 20 and 60%. The 127 samples which were normal in accordance with the immunoblotting method also gave normal activities of >50% in the method according to the invention. In summary, the results depicted in FIG. 4 verify the good agreement of the novel method with the conventional immunoblotting method and thereby prove that the conventional and very elaborate immunoblotting can be replaced, in accordance with the invention, by measuring VWF-mediated platelet aggregation. The method according to the invention is reproducible as is shown by the very small error limits within a test series and between different test series.

Clinical Application of the Method According to the invention

Figure 5:
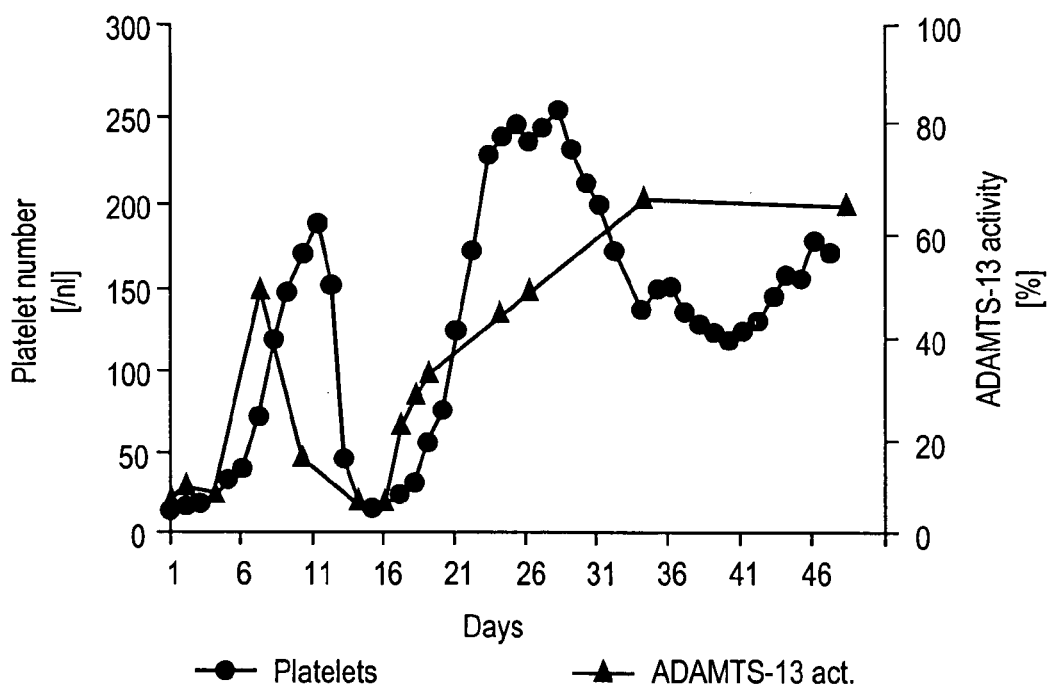
FIG. 5 is a graphical illustration of the ADAMTS-13 activity and platelet number for an exemplary patient subjected to plasmapheresis sessions over the course of the treatment.

It was possible to demonstrate the clinical applicability of the novel method by the measurement results which were obtained on 51 patients, with 22 attacks of acute TTP, and also other thrombotic, thrombocytopenic and/or hemolytic diseases, being investigated. A severe deficiency of ADAMTS-13 activity was only observed in patients suffering from acute classical TTP. Patients with low inhibitor concentrations reacted to the plasma substitution with an increase in ADAMTS-13 activity whereas there was no measurable increase in ADAMTS-13 activity in patients with high inhibitor concentrations even though the plasma substitution therapy led to clinical remission. The course of ADAMTS-13 activity in the case of a female patient having a low inhibitor concentration (0.7 U/ml) on admission is shown in FIG. 5 by way of example. The patient was successfully treated with a total of 36 plasmapheresis sessions over a period of 50 days. After an early relapse on day 14, the plasma therapy leads to a consistent increase in ADAMTS-13 activity. This increase is closely associated with the increase in platelets, which are depicted by the circles in FIG. 5. The figure makes it clear that the clinical course of the TTP episode can be mirrored by the ADAMTS-13 activity, as determined using the method according to the invention.

The examples demonstrate that the diagnostic method according to the invention makes it possible to measure the VWF-cleaving protease activity of ADAMTS-13. Comparison of the method according to the invention with the known immunoblotting method demonstrates the accuracy of the method according to the invention. The method according to the invention is reproducible and, in contrast to the conventional immunoblotting method, does not require any specialized laboratory equipment or special knowhow. It is preferably carried out overnight, with it also being possible to shorten the incubation time down to a few hours or minutes. The method according to the invention is less time-consuming than the immunoblotting.

The diagnostic method according to the invention can be used to determine ADAMTS-13 activity rapidly and reliably in any normally equipped coagulation laboratory. This makes it possible, in particular, to diagnose TTP rapidly and consequently to begin therapy immediately, something which is essential for successfully treating an acute episode. Beginning therapy at an early stage lowers the number of plasma substitution treatments which are required, with this very substantially lowering the costs of the therapy.

The invention claimed is:

1. A diagnostic method for determining the von Willebrand factor (VWF)-cleaving activity of ADAMTS-13 in a test medium, the method comprising the following steps:
   a) incubating art ADAMTS-13-free VWF with urea to form urea treated VWF,
   b) providing a test medium comprising unquantified ADAMTS-13,
   c) adding from 0.5 to 5 U per ml of said ADAMTS-13-free, urea treated von Willebrand factor to the test medium to form a reaction medium,
   d) incubating the reaction medium,
   e) adding platelets to the incubated reaction medium, and
   f) quantifying the ADAMTS-13 activity based on the reduction in the VWF-mediated aggregation of the added platelets in the incubated reaction medium.

2. A diagnostic method for determining the VWF-cleaving activity of ADAMTS-13 in a test medium, the method comprising the following steps:
   a) aggregating platelets by incubating the platelets with ADAMTS-13-free von Willebrand factor (VWF),
   b) providing a test medium comprising an unquantified ADAMTS-13 activity,
   c) adding the test medium to the aggregated platelets, and
   d) quantifying the ADAMTS-13 activity base on the dissociation of the platelet aggregates.

3. The method as claimed in claim 1, wherein the method is carried out in the presence of ristocetin.

4. The method as claimed in claim 1, in which the reduction in the VWF-mediated aggregation of platelets is determined using a calibration curve, with normal human plasma which has been diluted with varying quantities of inactivated normal human plasma being used for constructing the calibration curve.

5. The method as claimed in claim 2, in which the dissociation of the platelets is determined using a calibration curve, with normal human plasma which has been diluted with varying quantities of inactivated normal human plasma being used for constructing the calibration curve.

6. The method as claimed in claim 1, wherein a serine protease inhibitor is used.

7. The method as claimed in claim 1, wherein the test medium is blood plasma, blood serum, saliva, cerebrospinal fluid, cell culture supernatant or cell extract.

8. A diagnostic kit, containing an ADAMTS-13-free VWF and platelets, as well as urea for pretreating the ADAMTS-13-free VWF.

9. The diagnostic kit as claimed in claim 8, wherein the ADAMTS-13-free VWF and the urea are present in one container.

10. The diagnostic kit as claimed in claim 8, wherein said kit additionally contains ristocetin.

11. The method as claimed in claim 2, wherein the method is carried out in the presence of ristocetin.

12. The method as claimed in claim 2, wherein a serine protease inhibitor is used.

13. The method as claimed in claim 2, wherein the test medium is blood plasma, blood serum, saliva, cerebrospinal fluid, cell culture supernatant or cell extract.

* * * * *

UNITED STATES PATENT AND TRADEMARK OFFICE
CERTIFICATE OF CORRECTION

PATENT NO. : 7,291,479 B2 Page 1 of 1
APPLICATION NO. : 10/519824
DATED : November 6, 2007
INVENTOR(S) : Boehm It is certified that error appears in the above-identified patent and that said Letters Patent is hereby corrected as shown below:

Claims

Column 11
Claim 1, Line 46, delete "art" insert -- an --

Column 12
Claim 2, Line 14, delete "base" insert -- based --

Signed and Sealed this

Third Day of June, 2008

JON W. DUDAS
*Director of the United States Patent and Trademark Office*